United States Patent [19]

Faul et al.

[11] Patent Number: 5,440,606
[45] Date of Patent: Aug. 8, 1995

[54] X-RAY SYSTEM CONTROL

[75] Inventors: David D. Faul, Erlangen; Hans-Joachim Greiner, Buckenhof; Gerd Wessels, Erlangen, all of Germany

[73] Assignee: Siemens Aktiengesellschaft, Munich, Germany

[21] Appl. No.: 231,348

[22] Filed: Apr. 21, 1994

Related U.S. Application Data

[63] Continuation of Ser. No. 130,164, Sep. 30, 1993, which is a continuation of Ser. No. 875,562, Apr. 27, 1992, abandoned, which is a continuation of Ser. No. 577,973, Sep. 4, 1990, abandoned, which is a continuation of Ser. No. 218,378, Jul. 13, 1988, abandoned.

[51] Int. Cl.$^6$ .................................................. H05G 1/64
[52] U.S. Cl. ........................................ 378/98; 378/115; 378/116
[58] Field of Search ........................... 378/98, 115, 116

[56] References Cited

U.S. PATENT DOCUMENTS

| 4,581,645 | 4/1986 | Beyers | 358/181 |
| 4,807,273 | 2/1989 | Haendle | 378/116 |

FOREIGN PATENT DOCUMENTS

| 245153 | 11/1987 | European Pat. Off. | 378/99 |
| 2594321 | of 1987 | France | 378/40 |

*Primary Examiner*—Craig E. Church
*Attorney, Agent, or Firm*—Lawrence C. Edelman

[57] ABSTRACT

An x-ray diagnostic system wherein verbal, hands-free data input is available to the user for communicating with the components of the system. The components of the system, which are interconnected via a signal transmission path, include a speech recognition system for data input and a communication device designed so that available and executed commands are reproduced thereby.

17 Claims, 2 Drawing Sheets

X-RAY SYSTEM CONTROL

This application is a continuation of Ser. No. 08/130,164 filed Sep. 30, 1993 now abandoned, which is a continuation of Ser. No. 07/875,562 filed Apr. 27, 1992 now abandoned, which is a continuation of Ser. No. 07/577,973 filed Sep. 4, 1990 now abandoned, which is a continuation of Ser. No. 07/218,378 filed Jul. 13, 1988 now abandoned.

BACKGROUND OF THE INVENTION

1. Field of the Invention

The invention relates to control of an x-ray system having an x-ray generator, an x-ray apparatus, an input system for data and a communication arrangement for the reproduction of data.

2. Description of the Prior Art

In x-ray diagnostic systems known in the art, the input of data, e.g. the input of exposure values, is accomplished with the aid of mechanically operable switching means, e.g. with the help of keys or rotary switches. During the operation of an x-ray diagnostic system the operator must occasionally have his/her hands free to attend to other life-threatening tasks, such as medically related procedures. Thus, the entry of data through the aid of manually operable switching means is accordingly disturbing. Additionally, it is disturbing to manually reposition various portions of the x-ray system during a diagnostic procedure at a time when the hands of the operator are more urgently needed for other medically related procedures.

The control of a dental work station for the treatment of patients through spoken commands is already known from German Patent Publication 30 32 693. The operator need not use his/her hands for implementing relatively simple and direct control actions in this case, e.g., position adjustment of the dental chair or light, which is of great advantage in view of the need for sterility in many medically related procedures.

It is an object of the invention to develop an x-ray system of the type having a data input and control system, such that simple communication between the user and the input system is possible for operation and control.

SUMMARY OF THE INVENTION

This object is achieved according to the principles of the invention by interconnecting the components of the x-ray system together via a signal transmission path for transmitting digitally-coded messages among the x-ray system components. The signal transmission path also interconnects with the x-ray system, a speech recognition system for data input and a communication device which is so controlled that the available and executed x-ray system commands are reproduced therewith. In a preferred embodiment of an x-ray system constructed according to the principles of the invention, feedback to the operator from the x-ray system (i.e., the x-ray generator and the x-ray apparatus) is possible via the communication device. That is, the communication device is preferably a video monitor controlled by signals from the x-ray system in such a manner that the operator determines from the monitor which commands are available and observes/monitors execution of the desired commands put to the system.

Additional information for the operator related to the available commands may follow in a loudspeaker system for the acoustic reproduction of these commands. In addition to the speech recognition system, mechanically operable switching means may also be provided which allow the execution of continuous control actions, for example, the control of mechanical movements of the x-ray system components. The loudspeaker system may also alert the operator to input errors and repeat the executed commands.

Other features and advantages of the invention will be apparent from the description of the preferred embodiments, and from the claims.

For a fuller understanding of the present invention, reference should now be made to the following detailed description of the preferred embodiment of the invention and to the accompanying drawing.

DETAILED DESCRIPTION OF THE INVENTION

Figure 1:
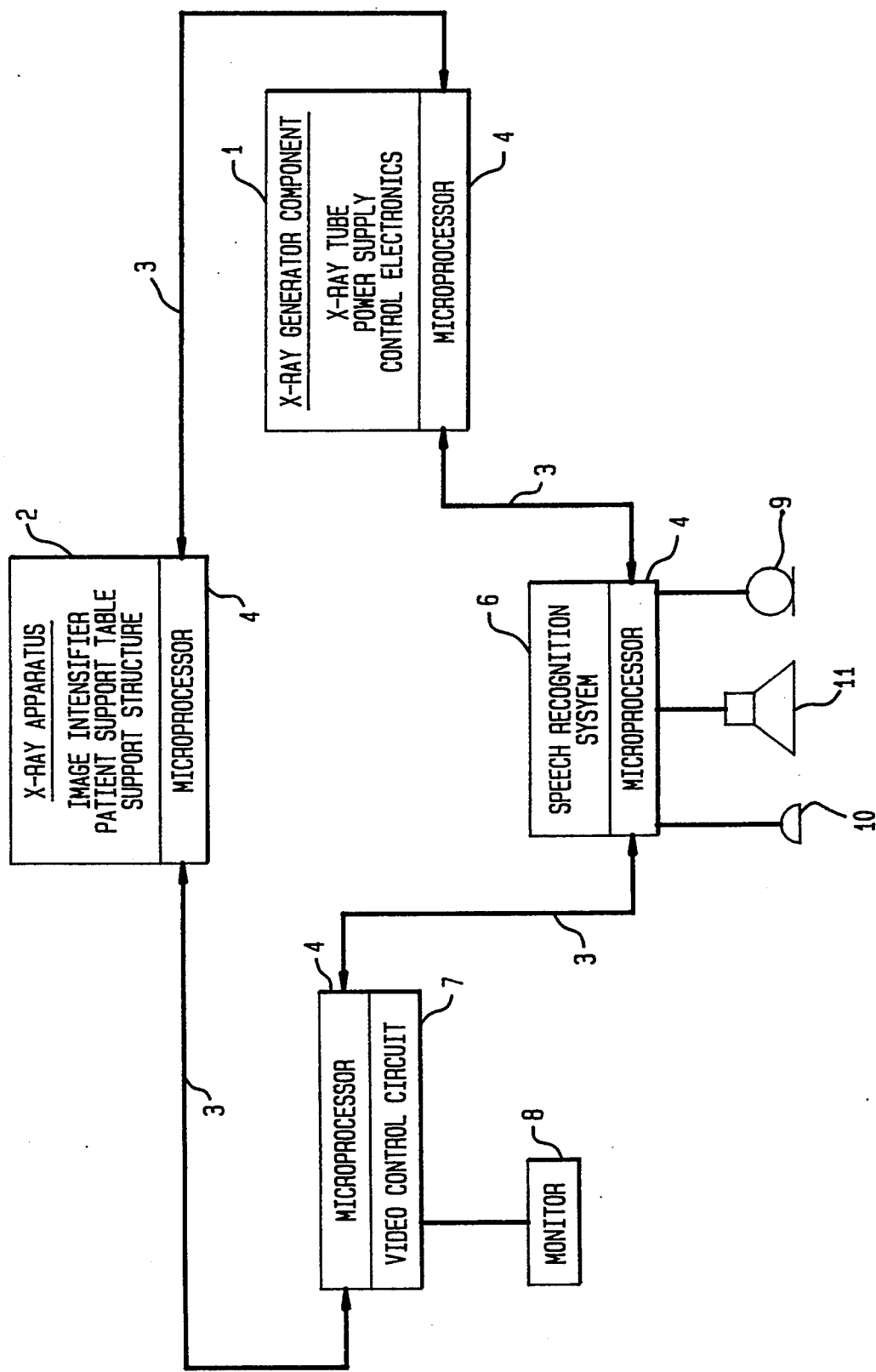
FIG. 1 illustrates an x-ray system constructed in accordance with the principles of the invention.

FIG. 1 shows an x-ray system having an x-ray generator component 1 (e.g., power supply, x-ray tube and control electronics) and additional x-ray apparatus 2 (e.g., image intensifier, patient support table and other support structures), which components are electrically connected with each other via a signal transmission path 3. The coupling of x-ray generator component 1 and additional x-ray apparatus 2 to signal transmission path 3 occurs via respective x-ray system interface devices 4. A speech recognition system component 6 and a video control circuit 7 are also serially connected to the x-ray system by signal transmission path 3 via their respective x-ray system interface devices 4. A monitor 8 controlled by video control circuitry 7 comprise a communication device for information reproduction.

Speech recognition system 6 (shown in detail in FIG. 2) is provided with a microphone 9 over which an operator of the system may input instructions and/or data (such as patient identification, date and system operation mode, etc.) in the form of spoken commands. An operator controlled foot switch 10 enables analog control procedures to be implemented, e.g., by varying the amount of pressure on foot switch 10. Speech recognition system 6 converts the spoken information entered via microphone 9 into machine compatible commands (i.e., digitally-coded messages) and/or data, which are entered into signal transmission path 3 via its x-ray system interface device 4, and which digitally-coded messages control the x-ray generator 1 and/or the x-ray apparatus 2 via their respective x-ray system interface device 4. Generally, interface devices 4 are microprocessor-based and connected for bi-directional communication with their respective system components.

Speech recognition system 6 is additionally connected to a loudspeaker system 11. Loudspeaker system 11 alerts the user to error messages (x-ray system errors), repeats executed commands and advises the operator of the system status, e.g., x-ray tube heat capacity is exceeded.

Figure 2:
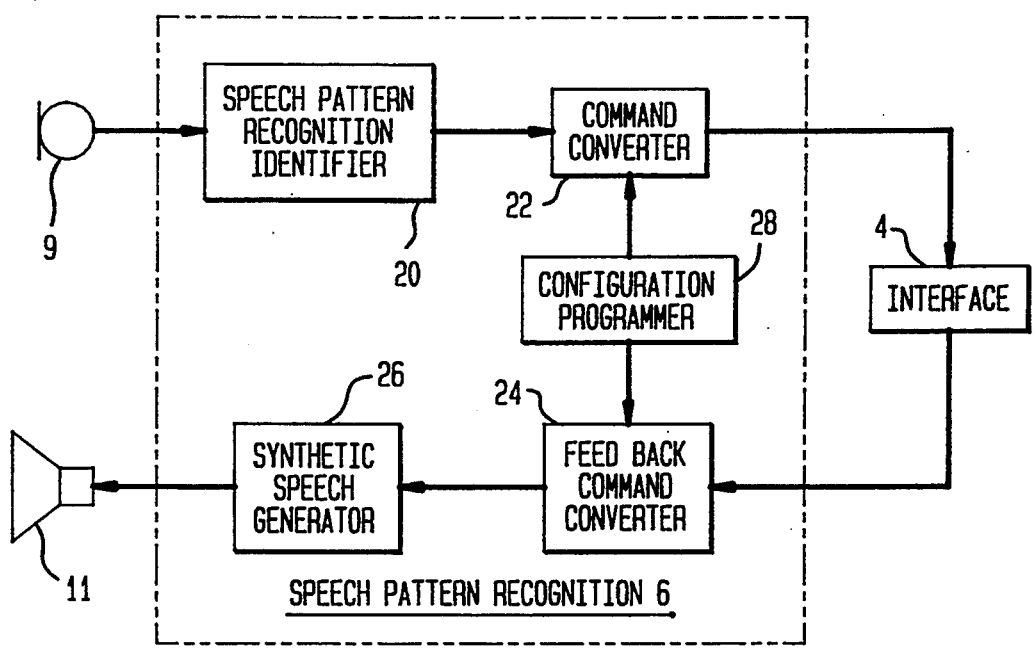
FIGS. 2 and 3 illustrate details of the x-ray system shown in FIG. 1.

As shown in FIG. 2, speech recognition system 6 includes a speech pattern recognition identifier 20 which receives the spoken commands from microphone 9 into a machine compatible (digital) form for further processing. The design of speech pattern recognition devices are known to those of ordinary skill in the art and therefore further description of this component is not deemed necessary. A command converter 22 converts the identified speech commands from pattern recognition identifier 20 into digitally-coded messages which are sent to appropriate ones of the x-ray system components via the interface devices 4 and interconnecting signal transmission path 3. Speech recognition system component 6 also includes a feedback command converter 24 which receives digitally-coded messages from the other components of the x-ray system via the interface device 4 associated with speech recognition system component 6, and provides a corresponding digital input to a synthetic speech generator 26 for causing loud speaker 11 to reproduce a synthetic speech answer in response to the received digitally-coded message. Both command converter 22 and feedback command converter 24 are freely programmable in their configuration with respect to converting identified speech patterns into digitally coded messages and vice versa via a configuration programmer 28. Speech recognition system 6 also includes a suitably programmed microprocessor (not specifically shown) for accomplishing converters 22 and 24 as well as generator 26, identifier 20 and programmer 28.

Therefore, when an interface device 4 receives a command from signal transmission path 3, originating from either one of the system operator or an interface device 4 of another component of the x-ray system, the command can be translated into a series of instructions directed to various sub-systems of its respective component (e.g., servocontrollers, position sensors and other regulation devices and circuits) for causing the command to be carried-out. For example, if an operator gave a spoken command to microphone 9, such as "intensifier out", interface device 4 of x-ray apparatus 2 would first cause apparatus 2 to determine the present position of the intensifier with respect to the patient, then reposition the intensifier support structure away from the patient, if needed, and finally retract the intensifier. Additionally, the system component advises its interface 4 of the status of the execution of the command, which information is then provided back to signal transmission path 3 and speech recognition system 6 and/or video control circuitry 7.

Video control circuitry 7, which controls monitor 8, holds data related to the available commands for speech controlled instructions and/or data input. The available commands are preferably displayed as words on monitor 8. Furthermore, video control circuitry 7 holds data, via its x-ray system interface 4, regarding the respective executed commands and/or data input via speech input commands, and also displays these commands and/or data on monitor 8 to the operator. By observing monitor 8, the operator can accordingly determine which commands he/she can input and/or which commands have already been executed.

Figure 3:
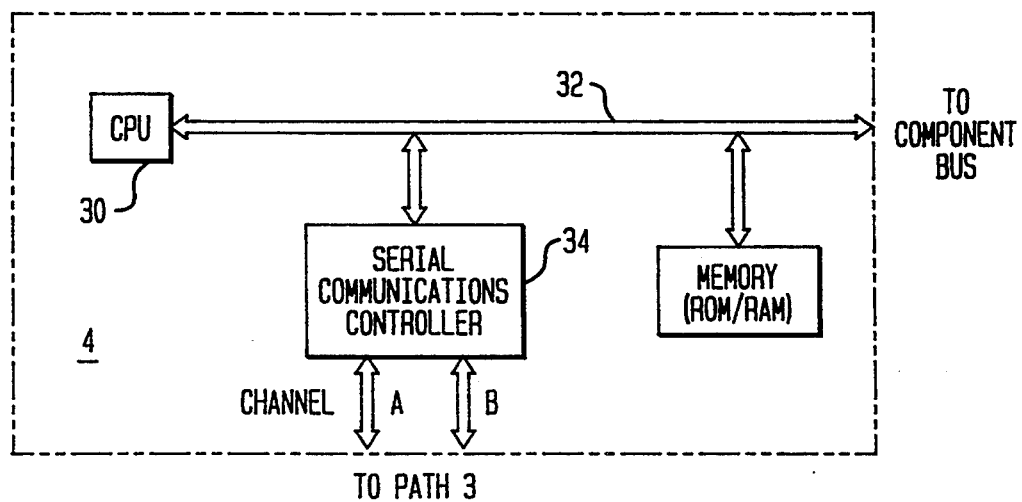

FIG. 3 illustrates the basic architecture of each interface device 4. Interface devices 4 communicate on the basis of two fiber optic cables which comprise the signal tranmission path 3. The cables serially connect the different components of the x-ray system together in the previously described operational manner. Each interface device 4 includes a microprocessor control (CPU) 30 which converts digitally-coded messages received from the signal transmission path into digitally-coded submessages which are sent to the respective x-ray system component via its internal bus 32. Additionally, digitally coded submessages from the component can also be transmitted via the CPU and component internal bus out to the signal transmission path for communication to the interface devices of other portions of the x-ray system. A serially communications controller 34 in each interface device 4 controls the flow of the digitally-coded messages between the signal transmission path 3 and the internal bus of each interface device.

Thus, there has been shown and described a novel apparatus for communicating with an x-ray system which fulfills all the objects and advantages sought therefore. The x-ray system control signals (digitally-coded messages) travel along a signal transmission path, which, at distributed locations, is coupled to the various x-ray system components. The x-ray system components each have a signal interface device, which is coupled to the signal transmission path in such a manner that the plurality of interface devices form a closed-loop configuration and the digitally-coded messages are passed serially among the interface devices. A great advantage of this arrangement is the extreme flexibility with respect to future modifications of the system. That is, existing systems can be easily modified by simply adding or subtracting system components in the signal transmission path without hardware modification (only simple to input software modifications may be necessary). Many changes, modifications, variations and other uses and applications of the subject invention will, however, become apparent to those skilled in the art after considering this specification and the accompanying drawing which disclose a preferred embodiment thereof. For example, signal transmission path 3, although shown as a closed circuit "loop," could be an open circuit interconnection, such as a cascade of the system components connected via a bi-directional bus or a star circuit connection of components to a central processor. Furthermore, the interconnections could be by fiber-optics. All such changes, modifications, variations and other uses and applications which do not depart from the spirit and scope of the invention are deemed to be covered by the invention which is limited only by the claims which follow.

What we claim is:

1. An X-ray system comprising:
a plurality of system components connected in series from a first to a last in a transmission path, whereby each of said system components can directly communicate with the other said system components in said transmission path, said system components including at least a speech recognition system for creating an adjustment signal in said transmission path corresponding to a spoken statement identifying a desired adjustment in said X-ray system, an X-ray generator component for selectively generating an X-ray beam, and an X-ray positioning component for controlling the spatial relationship between said X-ray beam and an object to be X-rayed, wherein said X-ray generator component and said X-ray positioning component directly communication with each other via said transmission path and operate in response to digitally-coded signals representative of the desired adjustment to provide said desired adjustment in response to said adjustment signal; and
a microprocessor control device included in each of said system components, the microprocessor control devices being coupled in series to each other via said transmission path, each said microprocessor control device being capable of generating a digitally-coded signal which is transmitted via said transmission path and/or responding to a digitally-coded signal in said transmission path which is communicated to said microprocessor control device via said transmission path;

wherein when a first system component addressed by said digitally-coded signal requires a response from at least one other system component to provide said desired adjustment, said microprocessor control device of said first system component generates a digitally-coded sub-message signal directed via said transmission path to communicate to said at least one other system component, for control of said at least one other system component by said digitally-coded sub-message signal.

2. The apparatus of claim 1, further including:

an indicator system serially coupled to said first and last system components for providing a visual and audible indication as to whether said adjustment signal properly corresponds to said spoken statement and whether said desired adjustment was successfully completed.

3. The X-ray system according to claim 2, wherein said indicator system includes a video display means, said video display means receiving signals transmitted in said transmission path and selectively converting said signals into text displayed on a video monitor.

4. The X-ray system according to claim 3, wherein said X-ray generator component includes at least an X-ray tube and an X-ray tube power supply that operate in a predetermined relationship, whereby when said spoken statement is directed to a desired adjustment in either said X-ray tube or said X-ray tube power supply, said microprocessor control device of said X-ray generator component decodes said adjustment signal, corresponding to said spoken statement, and generates instruction signals that operate to adjust both said X-ray tube and said X-ray tube power supply to achieve said desired adjustment and maintain said predetermined relationship.

5. The X-ray system according to claim 4, wherein said X-ray positioning component includes at least an image intensifier and a support table for said object being X-rayed that operate in a second predetermined relationship, whereby when said spoken statement is directed to a desired adjustment in either said image intensifier or said support table, said microprocessor control device of said X-ray positioning component decodes said adjustment signal, corresponding to said spoken statement, and generates second instruction signals that operate to adjust both said image intensifier and said support table to achieve said desired adjustment and maintain said second predetermined relationship.

6. The X-ray system according to claim 5, wherein each microprocessor control device of each said system components selectively generates status signals in said transmission path corresponding to the status of said system components performing said desired adjustment and selectively generates an accomplished signal in said transmission path when said desired adjustment is complete.

7. The X-ray system according to claim 6, wherein said status signals and said accomplished signal are selectively converted to text displayed on said video monitor by said video display means.

8. The X-ray system according to claim 7 further including a synthesized speech generator coupled in series to said transmission path, said synthesized speech generator selectively converting at least said adjustment signal, said status signals and said accomplished signal into synthesized speech corresponding to the signals.

9. In an X-ray system having a plurality of system components which control the operating parameters of said X-ray system and wherein each of said system components contains a microprocessor coupled in series along a common transmission path, a method of audibly adjusting said operating parameters comprising the steps of:

issuing a voice command directed toward a needed adjustment requiring control in at least one operating parameter which will require control of at least two system components in order to be carried out;

generating a digitally coded adjustment signal in said transmission path corresponding to said voice command, said adjustment signal being representative of said needed adjustment;

receiving said adjustment signal by one of said system components, which component microprocessor generates control signals for controlling the one system component, and also generates a sub-adjustment signal which is applied to said transmission path; and receiving said sub-adjustment signal by another of said at least two system components, which component microprocessor generates control signals for controlling said another system component in order to complete the needed adjustment.

10. The method according to claim 9, further including the step of verifying said adjustment signal properly corresponds with said voice command.

11. The method according to claim 10, further including the step of verifying said needed adjustment has been performed by said system components.

12. The method according to claim 11, further including the step of generating status signals in said transmission path corresponding the status of said system components performing said needed adjustment.

13. The method according to claim 12, further including the step of generating an accomplished signal in said transmission path when said system components have accomplished said needed adjustment.

14. The method according to claim 13, wherein said steps of verifying said adjustment signal and verifying said needed adjustment includes converting said adjustment signal and said accomplished signal into text displayed on a video monitor.

15. The method according to claim 14, wherein said steps of verifying said adjustment signal and verifying said needed adjustment further includes converting said adjustment signal and said accomplished signal into corresponding words of synthesized speech.

16. The method according to claim 15 wherein said step of generating a digitally coded adjustment signal in said transmission path includes issuing said voice command into a voice recognition system serially connected to said microprocessor of each said system component via said transmission path.

17. The method according to claim 16, wherein said systems components include at least an X-ray generator component for selectively generating an X-ray beam and an X-ray positioning component for controlling the spatial relationship between said X-ray beam and an object to be X-rayed, and wherein said X-ray generator component and said X-ray positioning component directly communicate with each other via said transmission path and operate in a coordinated manner to provide said desired adjustment in response to said adjustment signal.

* * * * *